(12) United States Patent
Kan et al.

(10) Patent No.: US 6,207,952 B1
(45) Date of Patent: Mar. 27, 2001

(54) WATER PHANTOM TYPE DOSE DISTRIBUTION DETERMINING APPARATUS

(75) Inventors: Toru Kan; Hideki Nonaka, both of Niihama (JP)

(73) Assignee: Sumitomo Heavy Industries, Ltd., Tokyo (JP)

( * ) Notice: Subject to any disclaimer, the term of this patent is extended or adjusted under 35 U.S.C. 154(b) by 0 days.

(21) Appl. No.: 09/131,874

(22) Filed: Aug. 10, 1998

(30) Foreign Application Priority Data

Aug. 11, 1997 (JP) .................................................. 9-216472

(51) Int. Cl.$^7$ .................................................. G01D 18/00
(52) U.S. Cl. .................................. 250/252.1; 250/370.07
(58) Field of Search ............................ 250/370.07, 252.1

(56) References Cited

U.S. PATENT DOCUMENTS 5,627,367 * 5/1997 Sofield ............................... 250/252.1
5,635,709 * 6/1997 Sliski et al. ........................ 250/252.1

FOREIGN PATENT DOCUMENTS 59-104086  7/1984  (JP) .
2-182271   7/1990  (JP) .

* cited by examiner

Primary Examiner—Constantine Hannaher
Assistant Examiner—Otilia Gabor
(74) Attorney, Agent, or Firm—Arent Fox Kintner Plotkin & Kahn, PLLC

(57) ABSTRACT

A sensor is inserted into a closed water tank filled with water to the brim and the closed water tank is fixed directly to a radiation beam irradiating section, and the sensor is moved freely with respect to a mounted frame used for fixation. Therefore, a rapid and accurate prediction of the actual dose distribution of radiation beam prior to radiation therapy can be conducted, even when the irradiating section is attached to a rotation gantry.

7 Claims, 8 Drawing Sheets

WATER PHANTOM TYPE DOSE DISTRIBUTION DETERMINING APPARATUS

BACKGROUND OF THE INVENTION

1. Field of the Invention

This invention relates to a water phantom type dose distribution determining apparatus, particularly to a water phantom type dose determining apparatus allowing a rapid and accurate determination of the dose distribution in water which is suitably used for predicting in advance the dose distribution of radiation beam, before radiation therapy dependent on the use of a proton radiation therapy device or the like is undertaken.

2. Description of the Prior Art

Conventional cancer therapy based on radiation of active rays uses X-rays, gamma rays, electron beams, fast neutron beams, etc. These active rays, as shown in FIG. 6, become the strongest at sites close to the surface of a patient, and thus may inflict damages on normal tissues close to the body surface when those rays are directed towards a cancer in a deeper part of the body. By the way, a proton or a particle which comes into being when a hydrogen atom has been removed of the electron, has a positive charge, and has a mass 1836 times as large as that of electron, can be accelerated under a high energy state by an accelerator to give a proton beam. The proton beam is characterized by having the maximum dose peak or a Bragg peak P at a certain depth from the body surface, and then declining rapidly to zero.

This is because, as the electric force a proton A exerts on electrons becomes large in proportion to its proximity to the latter, when the proton has a high kinetic energy and runs at a high speed, the time for the proton to interact with nearby electrons is short, and ionization is small in magnitude, but, when it loses the kinetic energy to nearly make a stop, the time for interaction becomes long and ionization rapidly increases in magnitude.

Thanks to this nature peculiar to protons, it is possible to apply proton beams for cancer therapy keeping normal cells other than a cancer comparatively free from damages, even if the cancer lies in a deeper part of the body. Further, as the radiation-based biological effect (RBE) of a proton beam is nearly equal to that of x-rays, the proton radiation therapy is advantageous in that it can make the most of knowledge and experience accumulated in the field of conventional X-ray radiation therapy. With these features, the proton radiation therapy device is being introduced as a therapy means to treat a cancer without removing any functional organs and encroaching on the quality of life.

In the radiation therapy of cancer, it is ideal to concentrate a lethal dose of active rays onto the cancer alone without inflicting any irreversible damages to nearby normal tissues. The Proton radiation therapy, as shown in FIG. 6, exploits the feature characteristic with protons that a proton beam incident on a substance gives the maximum dose or Bragg peak P just before it ceases to move. Namely the therapy in question aims at achieving this ideal by covering only the cancerous lesion with that Bragg peak.

By the way, protons obtained from an accelerator are in the form of a slender beam, and its energy is constant (the depth of Bragg peak is also constant). On the other hand, cancerous lesions are varied in size and have complex shapes, and their depths in the body are not constant. Further, the density of tissues through which a proton beam must pass is not constant neither. Accordingly, to achieve an effective radiation therapy, it is necessary to (1) enlarge the proton beam to have a sufficient width to cover the whole cancer lesion in one radiation; (2) adjust the beam energy according to the depth of lesion; (3) give a sufficient energy distribution in depth so that the whole cancer lesion having a certain depth can receive a uniform irradiation; and (4) make corrections according to the irregularities in contour of the lesion, and in density of the tissues through which the proton beam must pass. To meet these requirements, a device as shown in FIG. 7 is introduced whereby an irradiation field is formed in accordance with the shape of a lesion to be radiated. To put it more specifically, a slender proton beam 20 transmitted to an irradiating section is passed through a scattering body 22 made of lead with a thickness of several millimeters to be converted into a wide beam 24 extending crosswise. Out of the wide beam 24 which widens in a conical form with the summit at the scattering body 22, picked up by a collimator described below is a portion which is close to the central axis and comparatively uniform in dose distribution. This beam gives an irradiation field of about ten and several centimeters in diameter necessary for therapy on a therapeutic platform below (not illustrated here). The widened beam 24 is incident on a fine degrader 26 which adjusts the maximum attainable depth in accordance with the depth of a lesion to be treated (for example, a tumor 12 in the patient's body 10). The fine degrader 26 is composed, for example, of two wedge-shaped acryl blocks 26a and 26b placed opposite to each other, and adjustment of overlaps of the two blocks 26a and 26b enables a continuous alteration of the thickness through which the proton beam must pass. The proton beam loses energy in accordance with the thickness through which it must pass, and thus the depth it can reach varies in accordance therewith. Thus, adjustment by means of this fine degrader 26 makes it possible for Bragg peak P shown in FIG. 6 to fall at the same depth at which the lesion requiring therapy lies.

The proton beam, after having passed the fine degrader 26, is incident on a ridge filter 28 which is introduced to confer an energy depth distribution AP to the proton beam in accordance with the thickness of tumor 12. The ridge filter 28 consists of metal rods placed in parallel like a series of steps which have different thickness with each other. Proton beams passing through the metal rods different in thickness have Bragg peaks P at different depths. Thus, expansion of the range of peaks or AP can be achieved by adjusting the width and height of those "steps" to give appropriate overlaps.

The proton beam, after having passed through the ridge filter 28, is incident on a block collimator 30 which roughly adjusts the planar form of proton beam. The reason why the block collimator 30 is introduced here for the adjustment of beam shape, in addition to a final collimator described later, is to prevent secondary radiation due to the block collimator from occurring close to the patient's body.

The proton beam, after having passed through the block collimator 30, is incident on a bolus 32 or a resin-made irregularly formed filter, for example, and receives corrections in accordance with the cross-sectional shape of tumor 12 at the maximum depth, and the irregularities of involved tissues. The shape of bolus is determined on the basis of the electron densities of nearby tissues determined from the contour line of tumor 12 and, for example, X-ray CT data of that tumor.

The proton beam, after having passed through the bolus 32, is incident on a final collimator 34 made of brass, for example, receives a final correction in accordance with the contour of planar shape of the tumor 12, and strikes the patient 10 as a therapeutic proton beam 36.

Prior to treatment, firstly, to check that the irradiation field is formed as initially designed, it is necessary to predict the actual dose distribution using a water phantom type dose distribution determining apparatus as shown in FIG. 8, which includes a water tank 42 equipped with a sensor 46 and filled with water 44 to simulate the absorption of active rays by the human body.

The conventional proton radiation therapy device is based on a horizontal or vertical static radiation, and, as the entire device including the irradiating section 120 is fixed rigidly, positioning of the device is determined manually each time experiment is undertaken: the water tank 42 has its top opened, and is placed on the treatment bed, or is placed on a wheeled cart 48.

With the conventional device, however, it is cumbersome to make a proper positioning, and properly maintain the level of water 44, and further water may spill while the water tank is being carried, to cause the water level to change. When the radiation therapy device is operated for actual treatments, it will be probably used at a frequency of once for every 20 minutes. Thus, checking the dose distribution by means of a water phantom type dose distribution determining apparatus must proceed rapidly. Further, as the device is handled by a physician or a radiological technician instead of an engineer, the apparatus must not require special techniques for its operation and must be easily manipulated. With the irradiating section 120 as shown in FIG. 1 (not publicly known) the inventors are designing in order to irradiate a properly shaped proton beam, the irradiating section 120 is mounted on a rotary irradiation chamber (to be referred to as gantry) rotatable round a therapeutic bed 200 on which a patient is fixed, and the irradiating section rotates 360° round the patient during use. Thus, as shown by the broken line of FIG. 8, the incident angle θ of proton beam with respect to the surface of water 44 in the water tank 42 varies during rotation, but the device must be so constructed as not to allow those altered angles to affect the measurement results of dose distribution.

SUMMARY OF INVENTION

This invention aims at providing a water phantom type dose distribution determining apparatus meeting above requirements and suitably applied to a proton radiation therapy device for medical use.

This invention solves above problems by providing a water phantom type dose distribution determining apparatus for determining the dose distribution in water of a radiation beam irradiated from a radiation beam irradiating section using a sensor placed in the water, which comprises: a closed water tank filled with water to the brim and containing the sensor therein; a mount means to attach the closed water tank to the radiation beam irradiation section; and a moving means to move at least the sensor with respect to the mount means. The moving means may move the sensor together with the closed water tank in the direction vertical to the radiation direction of radiation beam, while it moves only the sensor in directions in parallel with the radiation direction of radiation beam.

According to this invention, it is possible to rapidly and easily determine the dose distribution of radiation beam prior to treatment. Particularly, as the closed water tank filled with water is used, the distance between the water surface and the sensor position remains constant even when the radiation beam irradiating section is mounted to a rotation gantry and is revolved to meet an actual radiation condition, and thus it is possible to accurately determine the dose distribution in accordance with the lesion of a patient to be treated. Further, water spilling does not occur while the water tank is moved; the water level therefore remains constant; and no monitoring of water surface is needed. Furthermore, the apparatus is advantageous in that attaching and detaching it to and from the radiation beam irradiating section is easy, and thus it is simple for handling.

BRIEF DESCRIPTION OF THE DRAWINGS

The preferred embodiments will be described below with reference to the drawings, wherein like elements have been denoted throughout the figures with like reference numerals, and wherein.

DESCRIPTION OF THE PREFERRED EMBODIMENTS

Figure 1:
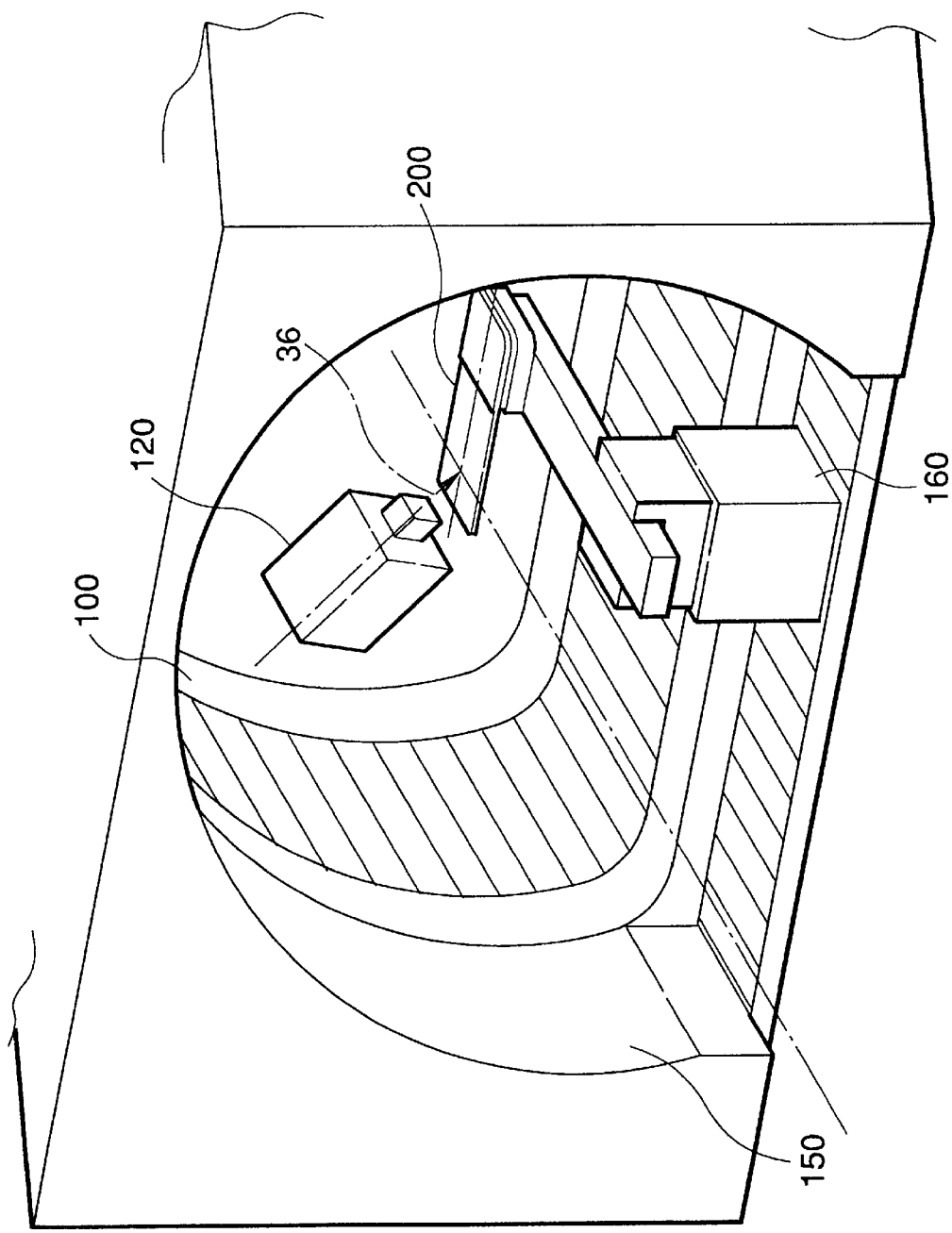
FIG. 1 is a perspective view illustrating how to the rotation gantry is mounted the radiation beam irradiating section to which is attached the water phantom type dose distribution determining apparatus of this invention.

Embodiment of this invention will be detailed below with reference to figures which are applied to a proton radiation therapy device having a rotation gantry 100 whereby an irradiating section 120 of a proton beam 36 rotate around a treatment bed 200 as shown in FIG. 1. In FIG. 1, 150 stands for a preparation room set up in front of the rotation gantry 100; and 160 for a bed moving unit to carry the bed 200 freely along six axes (X, Y, and Z, and θx, θy, and θz) from the preparation room 150 into the rotation gantry 100.

Figure 2:
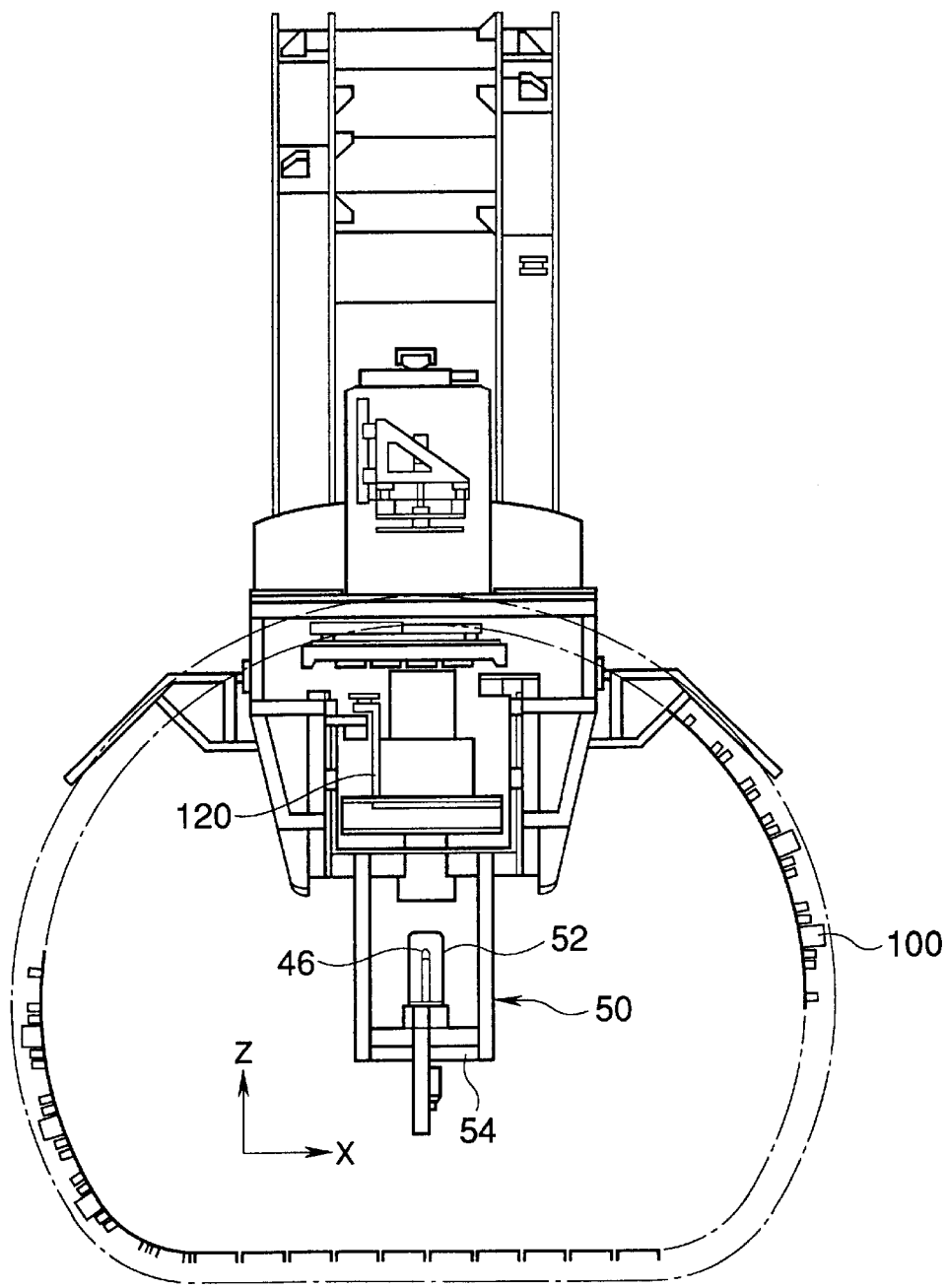
FIG. 2 is a front view illustrating how an embodiment of this invention is attached to the tip of the radiation beam irradiation section.

FIG. 2 shows how a water phantom type dose distribution determining apparatus 50 of this embodiment is attached to the tip (the lowermost end in the figure) of the irradiating section 120.

The water phantom type dose distribution determining apparatus 50 of this embodiment comprises a cylindrical closed water tank 52 filled with water to the brim and receiving a sensor 46 inserted from the bottom; a mount frame 54 to attach the closed water tank 52 to the irradiating section 120; and a moving mechanism 60 which moves the sensor 46 together with the closed water tank 52 with respect to the mount frame 54 in directions vertical to the radiation direction of proton beam 36 (lateral directions, and directions vertical to the surface of FIG. 2), and moves only the sensor 46 in the closed water tank 52 in directions in parallel with the radiation direction of proton beam 36 (up and down direction of FIG. 2).

Figure 3:
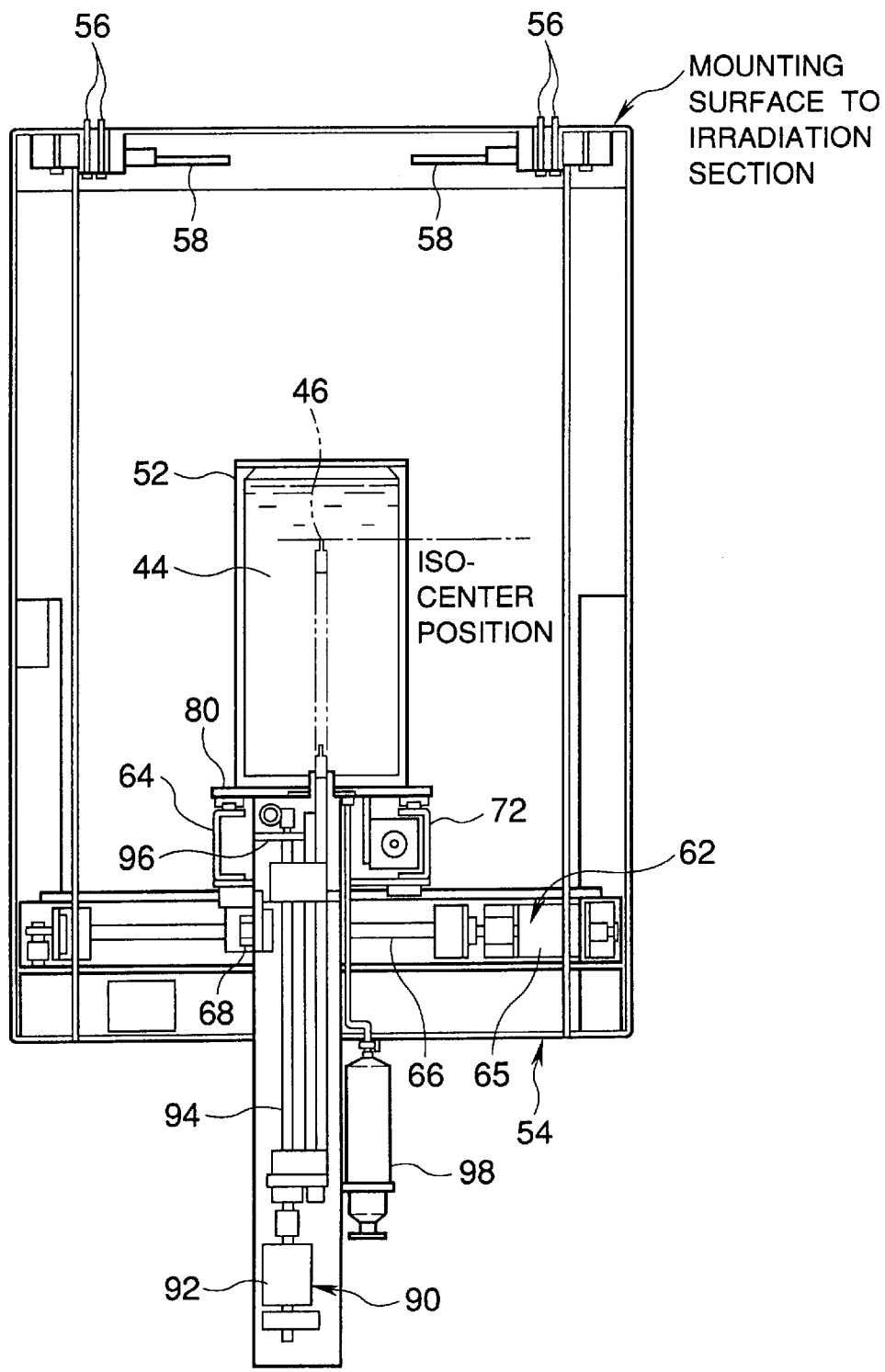
FIG. 3 is an enlarged front view of the dose distribution determining apparatus of the above embodiment.

As shown in detail in FIG. 3, the mount frame 54 has positioning pins 56 which establish a proper positioning by penetrating holes (not illustrated in FIG. 3) prepared on the mounting surface of the irradiating section 120, and one-touch levers 58, for example, four in number, which fix the mount frame 54 to the irradiating section 120 by clamping through simple one-way operations.

Figure 4:
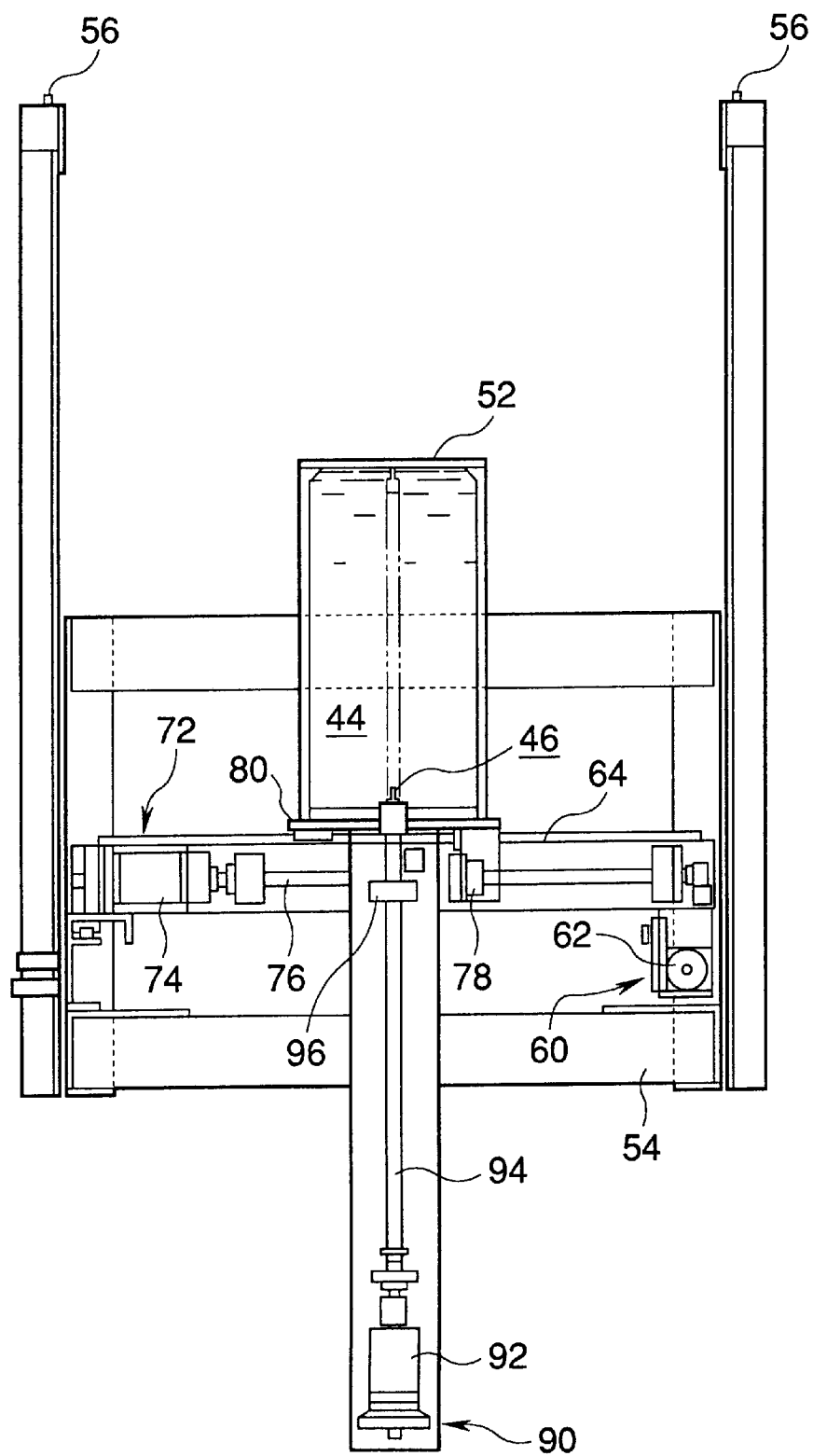
FIG. 4 is an enlarged side view of the same apparatus.
Figure 5:
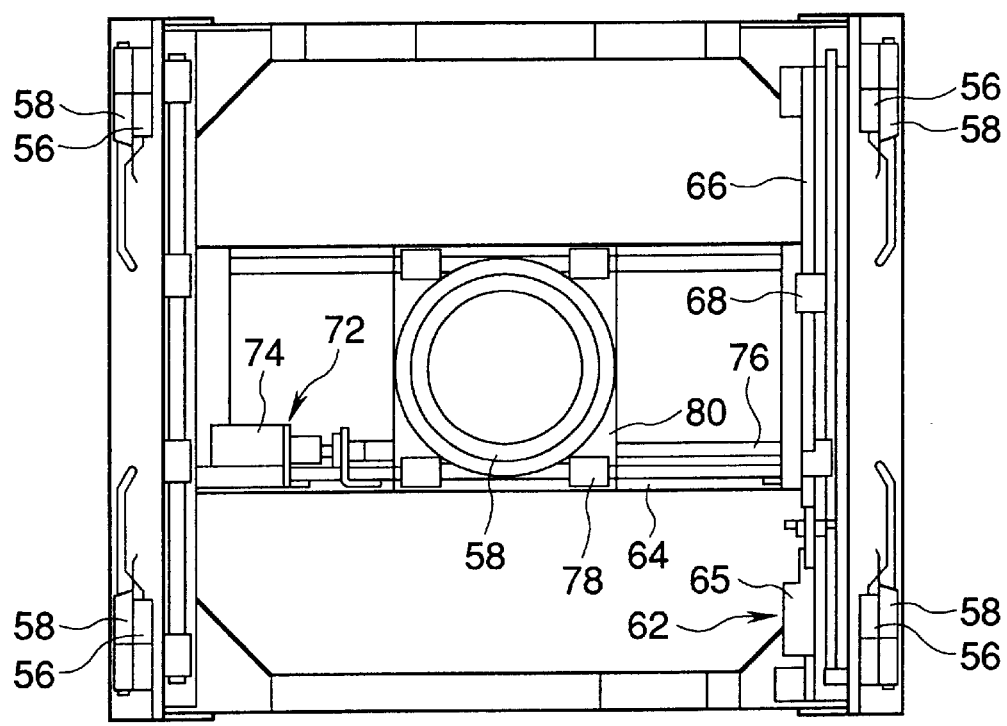
FIG. 5 is a sectional view of the same apparatus.
Figure 6:
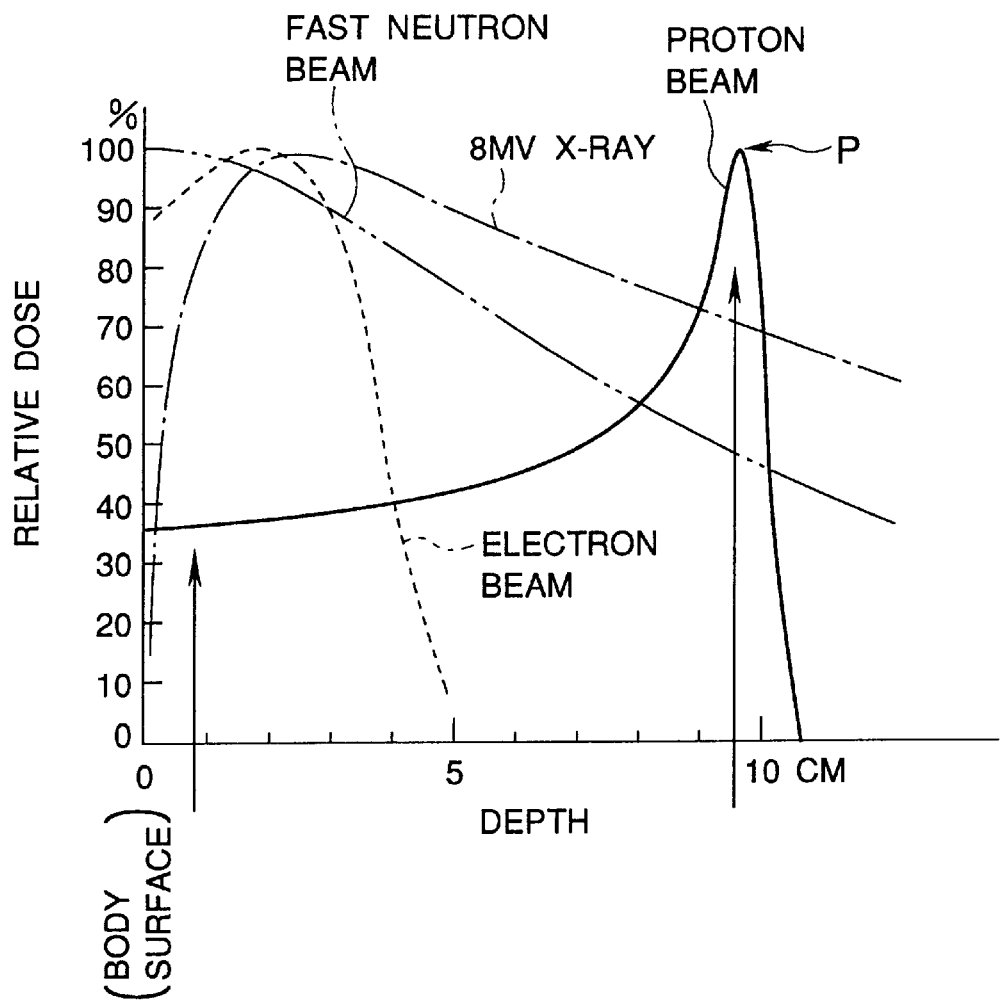
FIG. 6 gives graphs for explaining the principle underlying proton radiation therapy.
Figure 7:
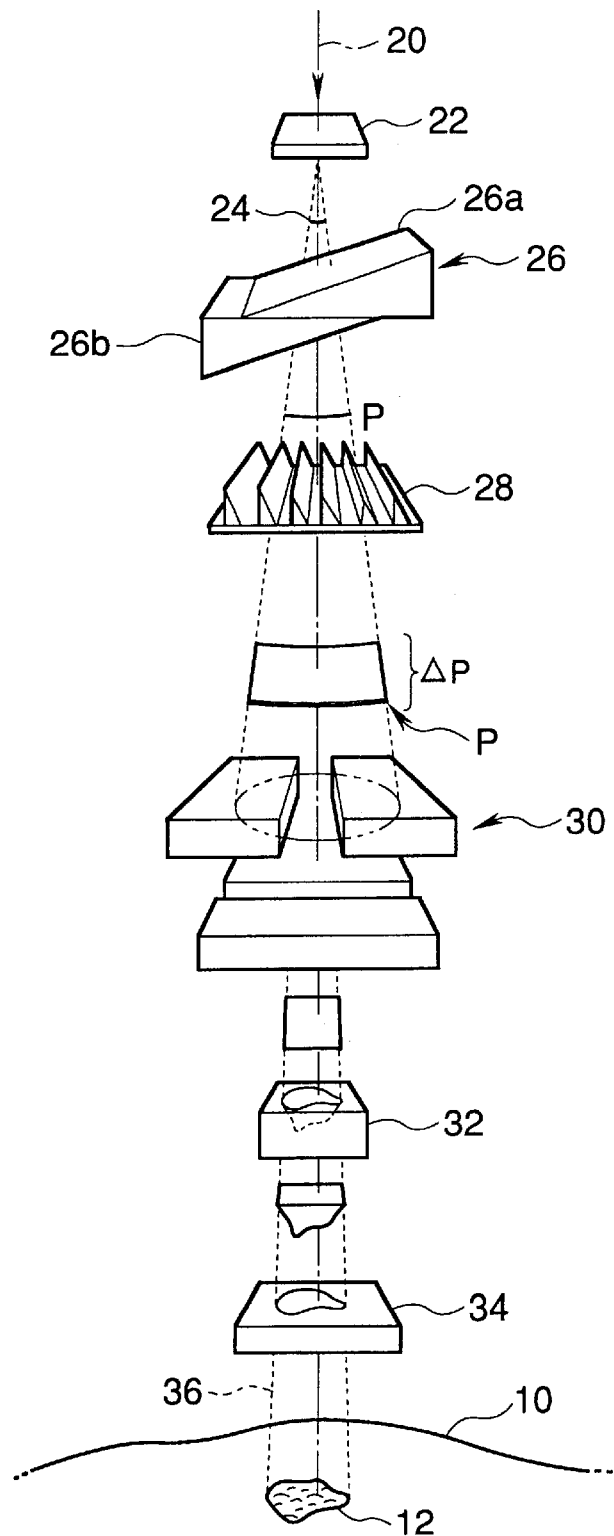
FIG. 7 is a perspective view illustrating the principle underlying the formation of an irradiation field in proton radiation therapy.
Figure 8:
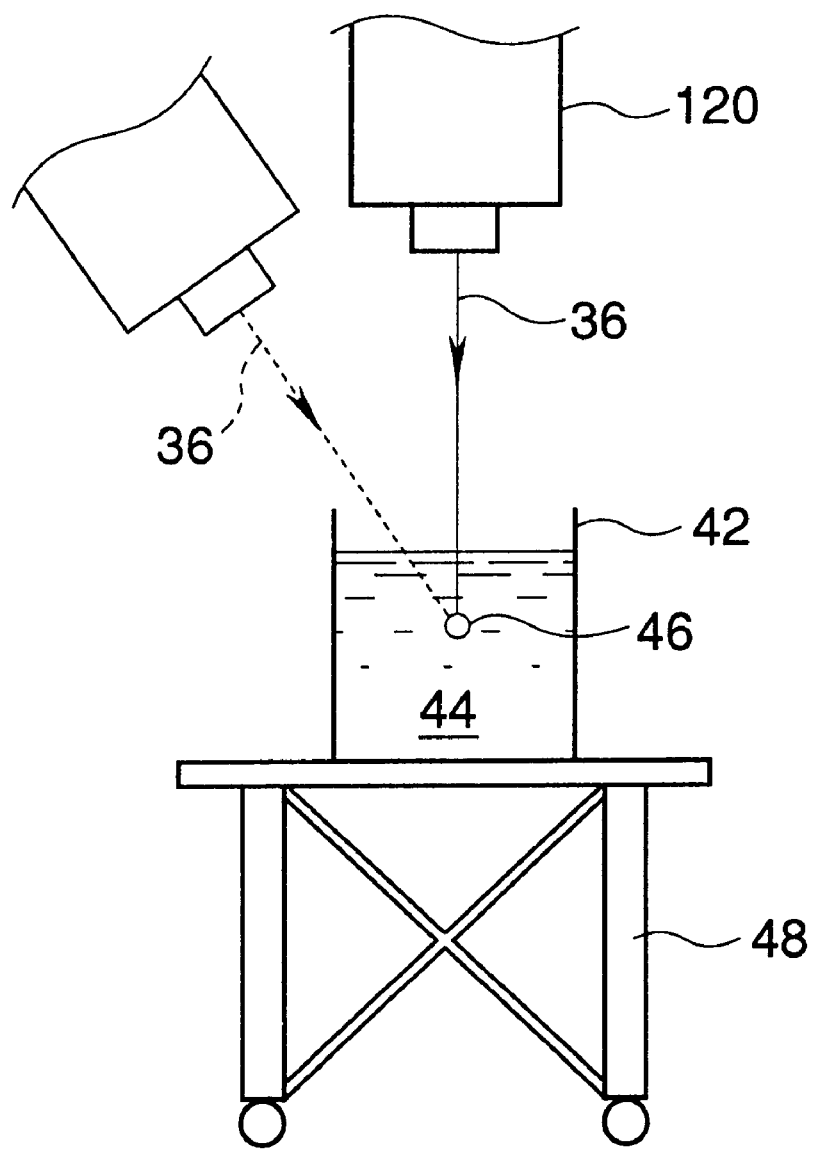
FIG. 8 is a sectional view illustrating the composition of a conventional water phantom type dose distribution determining apparatus, and problems inherent therewith.

As shown in detail in FIGS. 3 to 5, the moving mechanism 60 comprises an X-axis driving device 62 to carry an X-direction moving frame 64 along X-axis (lateral directions of FIG. 3) with respect to the mount frame 54; a Y-axis driving device 72 to carry a Y-direction moving frame 80 along Y-axis with respect to the X-direction moving frame 64 (directions vertical to the surface of FIG. 3), and a Z-axis driving device 90 to move the sensor 46 from the bottom surface of the closed water tank 52 attached to the Y-direction moving frame 80 to a specified depth (for example to a level flush with the iso-center position).

As shown in detail in FIG. 3, the X-axis driving device 72 has an electric motor 65 containing, for example, a decelerator, and fixed to the mount frame 54, a feed screw 66 which is driven into rotation by the electric motor 65; and a nut 68 to move the X-direction moving frame 64 along X-axis direction by engaging with the feed screw 66.

As shown in detail in FIG. 4, the Y-axis driving device 72 has an electric motor 74 fixed to the X-direction moving frame 64 and containing, for example, a decelerator, a feed screw 76 which is driven into rotation by the electric motor 74, and a nut 78 which moves the Y-direction moving frame 80 along Y-axis direction by engaging with the feed screw 76. As shown in detail in FIG. 4, the Z-axis driving device 90 has an electric motor 92 fixed to the Y-direction moving frame 80 and containing, for example, a decelerator, a feed screw 94 which is driven into rotation by the electric motor 92; and a nut 96 to move the sensor 46 along Z-axis direction by engaging with the feed screw 94.

In FIG. 3, 98 stands for a cylinder to adjust the volume of water in the closed water tank 52 which varies according to how deep the tank is moved along Z-axis.

Prior to the dose distribution measurement, the mount frame 54 is properly positioned with respect to the irradiating section 120 by means of the positioning pins 56, and then the mount frame 54 is attached to the irradiating section 120 through the works of one-touch levers 58.

Then, electric motors 64, 74 and 92 connected with X-, Y- and Z-axis driving devices 62, 72 and 90 respectively are put into rotation to move the sensor 46 at desired positions, and the dose distribution measurement is undertaken.

In this embodiment, thanks to the positioning pins 56, the mount frame 54 can be accurately attached with respect to the irradiating section 120, and thus highly reproducible results can be obtained.

Further, as the mount frame 54 is fixed to the irradiating section 120 through the works of one-touch levers 58, attaching and detaching the mount frame 54 to and from the irradiating section 120 are easy to manipulate.

Furthermore, as the sensor 46 can be freely moved to a desired depth in the closed water tank 52 by means of the Z-axis driving device 90, it is quite easy to alter the distance between the water surface and the sensor, or the distance corresponding with that from the surface of a patient's body to his/her lesion to be treated.

Still further, as X- and Y-axis driving devices 62 and 72 are introduced to move the closed water tank 52 itself, the constitution of X- and Y-axis driving devices is simple. Moreover, it is also possible to freely move only the sensor 46 throughout the closed water tank 52 along three coordinate axes of X-, Y- and Z-axis.

In the above-described embodiment, this invention is applied to a proton radiation therapy system including an irradiating section installed in a rotation gantry 100, but the applicable field of this invention is not limited to above, but apparently can be applied with the same profit to an irradiating section rigidly fixed to a fixed beam chamber, or to other radiation therapy systems based on the use of X-rays, electron beams, or the like.

What is claimed is:

1. A water phantom type dose distribution determining apparatus for determining the dose distribution in water in a radiation beam irradiated from an irradiating section using a sensor placed in water, comprising:

a closed water tank filled with water to brim and having the sensor inserted thereinto;

a mount means to attach the closed water tank to the irradiation section, the irradiation section being located outside of the closed water tank;

a moving means to move at least the sensor with respect to the mount means wherein the distance between the water surface and the sensor can be adjusted by the moving means.

2. The dose distribution determining apparatus as set forth in claim 1 wherein the closed water tank is attached to tip of the irradiation section, and the sensor is inserted into the closed water tank from opposite side.

3. The dose distribution determining apparatus as set forth in claim 2 which further comprises a cylinder to adjust volume of water which varies according to insertion depth of the sensor.

4. The dose distribution determining apparatus as set forth in claim 1 wherein the mount means has a positioning means.

5. The dose distribution determining apparatus as set forth in claim 1 wherein the mount means further comprises a clamping mechanism having one-touch levers.

6. A water phantom type dose distribution determining apparatus for determining the dose distribution in water of a radiation beam irradiated from an irradiating section using a sensor placed in water, comprising:

a closed water tank filled with water to brim and having the sensor inserted thereinto;

a mount means to attach the closed water tank to the irradiation section, the irradiation section being located outside of the closed water tank;

a moving means to move at least the sensor with respect to the mount means;

wherein the moving means moves the sensor together with the closed water tank in directions vertical to the radiation direction of the radiation beam, and moves the sensor alone in directions in parallel with the radiation direction of the radiation beam.

7. The dose distribution determining apparatus as set forth in claim 6 wherein the moving means moves the closed water tank in two dimensional directions vertical to the radiation direction of the radiation beams.

* * * * *